(12) United States Patent
Miyake et al.

(10) Patent No.: US 7,338,635 B2
(45) Date of Patent: Mar. 4, 2008

(54) ANALYZING APPARATUS

(75) Inventors: Takashi Miyake, Nishinomiya (JP); Noriyuki Kitamura, Nishinomiya (JP)

(73) Assignee: Furuno Electric Company, Limited, Nishinomiya-shi (JP)

( * ) Notice: Subject to any disclaimer, the term of this patent is extended or adjusted under 35 U.S.C. 154(b) by 855 days.

(21) Appl. No.: 10/242,756

(22) Filed: Sep. 13, 2002

(65) Prior Publication Data
US 2003/0053933 A1    Mar. 20, 2003

(30) Foreign Application Priority Data
Sep. 14, 2001    (JP)    ............... 2001-279300
Sep. 28, 2001    (JP)    ............... 2001-298775

(51) Int. Cl.
*B32B 5/02*    (2006.01)

(52) U.S. Cl. ............... 422/63; 422/65; 422/66; 422/67; 422/99; 422/100; 422/101; 422/243; 436/180

(58) Field of Classification Search ............ 422/63–67, 422/99–101, 243; 436/180
See application file for complete search history.

(56) References Cited

U.S. PATENT DOCUMENTS 4,919,887 A * 4/1990 Wakatake ............... 422/67

FOREIGN PATENT DOCUMENTS

EP    0 074 102 A1    3/1983
EP    0 195 893 A1    10/1986

* cited by examiner

*Primary Examiner*—Jill Warden
*Assistant Examiner*—Jyoti Nagpaul
(74) *Attorney, Agent, or Firm*—Birch, Stewart, Kolasch & Birch, LLP

(57) ABSTRACT

An analyzing apparatus has a partition dividing the interior of a housing into a lower space accommodating a power supply/control unit which generates heat and a duct and an upper space accommodating other units. Heat generated by cooling devices is exhausted to the exterior of the housing through the duct while the heat generated by the power supply/control unit is otherwise exhausted to the exterior. This construction makes it possible to achieve an improved heat exhaust efficiency and efficient cooling of a reaction unit provided in the upper space of the housing. A cover holding mechanism includes at least one each spring cam hinge and friction hinge. The spring cam hinge is formed of a cam mechanism and a spring which together produce a force acting on a cover in its opening or closing direction, the direction of the force reversing at a specific angle of the cover halfway between its open and closed positions, while the friction hinge produces a frictional force which works to hold the cover at any position between its open and closed positions. The spring produces an auxiliary force to facilitate cover-opening action, and the force produced by the spring works together with the frictional force to prevent the falling of the cover during its closing motion, enabling smooth cover-opening and closing actions.

4 Claims, 11 Drawing Sheets

ANALYZING APPARATUS

BACKGROUND OF THE INVENTION

1. Field of the Invention

This invention relates to an analyzing apparatus to be used for performing biochemical analyses or the like.

2. Description of the Prior Art

A conventional analyzing apparatus used for performing biochemical analyses generally comprises a reagent unit for storing one or more kinds of reagents, a sample storage unit for storing samples and a reaction unit for causing a reaction between the samples and reagents. These units are normally contained in a housing provided with a cover which can be easily opened and closed. It is necessary to maintain the reagents at low temperatures in the housing. For this purpose, a Peltier element is used to configure each cooling device, for example. It is also necessary to provide a power supply/control unit for controllably turning a tray which is provided for turning the reagent unit, the sample storage unit and the reaction unit.

In the analyzing apparatus thus constructed, the cooling effect produced by cooling devices for cooling the reagent unit is impeded by heat generated by the cooling devices themselves and the power supply/control unit. An approach commonly taken in the conventional analyzing apparatus to cope with this heat problem is to remove exhaust heat to the exterior of the housing by use of an exhaust device.

On the other hand, the analyzing apparatus is provided with a cover holding mechanism which enables free open/close actions with a capability to stably hold the swingable cover at any desired position, such as the open position, the closed position, or any position halfway between the open and closed positions. This kind of cover holding mechanism is made of a gas damper mechanism, a spring-cam-hinge mechanism employing a cam mechanism and a spring, or a friction-hinge mechanism using frictional resistance, for example.

Provided with a hinge attached to a supporting edge of the swingable cover, the gas damper mechanism holds the cover at a desired position between its open and closed positions with reaction force. The gas damper mechanism is a cover holding mechanism which also produces an auxiliary force to facilitate cover-opening action, prevents the falling of the cover during its closing motion, and smoothens opening and closing motions of the cover due to sliding friction produced by a gas damper.

The spring-cam-hinge mechanism employing a spring-loaded cam mechanism is disclosed in Japanese Unexamined Patent Publication No. 10-78027, for example, in which the cover is held in a desired position by a combination of the spring and the cam mechanism. The spring produces an auxiliary force to facilitate cover-opening action and prevents the falling of the cover during its closing motion.

The friction-hinge mechanism employing a friction hinge, of which example is disclosed in Japanese Unexamined Patent Publication No. 2000-27846, holds the cover at a desired position between its open and closed positions by the frictional resistance and prevents the falling of the cover during its closing motion.

The aforementioned conventional analyzing apparatus has been associated with a problem that it is difficult to efficiently remove exhaust heat to the exterior of the housing because various units are enclosed in the single housing.

As the individual units are together contained in the housing, heat generated by the cooling devices and the power supply/control unit tends to collect around the reagent unit and such waste heat must be removed from inside the entire housing by means of the exhaust device, resulting in a poor heat exhaust efficiency. Although it would be possible to provide a heat exhausting device, such as a heat pipe, to allow for efficient heat exhaust operation, such a provision is generally expensive and makes the construction of the analyzing apparatus too complex.

The gas damper mechanism requires two kinds of sub-mechanisms, that is, the gas damper and the hinge. The gas damper requires a relatively broad dedicated space to ensure a large stroke of motion. The gas damper is also expensive and should be periodically replaced as its reaction force considerably decreases due to aging. Another problem of the gas damper mechanism is that high-pressure gases contained in the gas damper eventually become an industrial waste product.

The spring-cam-hinge mechanism employing the spring-loaded cam mechanism has a safety-related problem, because the cover would suddenly open when the direction of force exerted by a cam changes.

The friction-hinge mechanism necessitates a large force to be exerted when opening the cover to act against the frictional resistance and the weight of the cover. In addition, when an operator closes the cover, the friction-hinge mechanism does not return a feeling the cover has been fully closed. Therefore, it might be necessary to additionally provide a lock mechanism to produce a tangible response.

SUMMARY OF THE INVENTION

In light of the foregoing, it is an object of the invention to provide an analyzing apparatus employing a housing of which internal space is divided into high-temperature and low-temperature areas to separately accommodate various units in order to achieve an improved heat exhaust efficiency and to ensure efficient functioning of a reagent unit cooling devices. It is another object of the invention to provide a cover holding mechanism which produces a force acting on a cover of an analyzing apparatus with a spring-cam-hinge mechanism, for instance, in cover-opening or closing direction, in which the force exerted by the cover holding mechanism performs the same function as a gas damper mechanism with a combination of a first hinge which produces a force whose direction is reversed at a specific angle of the cover halfway between its open and closed positions and a second hinge which produces a force acting in a direction opposite to the cover-opening or closing direction of the friction-hinge mechanism.

In one form of the invention, an analyzing apparatus comprises a reagent unit, a cooling device for cooling the reagent unit, a sample storage unit, a reaction unit, a power supply/control unit for feeding electric power to and controlling the individual units and device, a housing enclosing the individual units and device, and a partition dividing the interior of the housing into an upper space and a lower space. The upper space of the housing accommodates the reagent unit, the sample storage unit, the reaction unit and the cooling device while the lower space of the housing accommodates the power supply/control unit and a duct for collecting exhaust heat generated by the cooling device, the duct and the power supply/control unit being connected to the exterior of the housing.

In the analyzing apparatus thus constructed, the interior of the housing is divided into the upper space (low-temperature area) for accommodating the units which should be held at low temperatures and the lower space (high-temperature area) for accommodating the duct and the power supply/ control unit which generates heat. In this construction, the heat generated by the cooling device is exhausted to the exterior of the housing without adversely affecting the reaction unit provided in the upper space of the housing. Also, the heat generated by the power supply/control unit that tends to become deposited in the lower space is exhausted to the exterior of the housing, making it possible to suppress adverse effects to the reaction unit in the upper space of the housing. Therefore, this construction of the invention makes it possible to achieve an improved heat exhaust efficiency and efficient cooling of the reaction unit provided in the upper space of the housing.

In one feature of the invention, the cooling device is provided with an exhaust fan for forcibly expelling exhaust air to the exterior of the housing through the duct.

In this construction, the heat generated by the cooling device is forcibly exhausted to the exterior of the housing, so that it is possible to achieve an improved heat exhaust efficiency and ensure efficient functioning of the reaction unit cooling device.

In another feature of the invention, the analyzing apparatus comprises more than one cooling device, wherein the duct is shared by multiple cooling devices.

In this construction, the heat generated by the multiple cooling devices is exhausted with high efficiency, enabling efficient functioning of the reaction unit cooling device.

In another feature of the invention, the lower space of the housing accommodates an exhaust fan for creating an air flow at least along the power supply/control unit.

In this construction, the heat generated by the power supply/control unit is forcibly exhausted to the exterior of the housing, so that it is possible to achieve an improved heat exhaust efficiency and ensure efficient functioning of the reaction unit cooling device.

In another feature of the invention, the analyzing apparatus further comprises at least two hinges provided between the housing and a cover covering a top surface of the housing, the hinges supporting the cover in a manner that the cover can be freely opened and closed and held at a desired position, wherein at least one of the hinges is a first hinge which produces a force acting on the cover in its opening or closing direction, the direction of the force reversing at a specific position of the cover, and at least another one of the hinges is a second hinge which produces a force acting on the cover in a direction opposite to the direction of its swing motion.

This construction employing a combination of the first and second hinges makes it possible take advantage of the earlier-mentioned three types of cover holding mechanisms, that is, the gas damper, spring-cam-hinge, and friction-hinge mechanisms. Specifically, the cover can be held in its open position with a combination of the forces produced by the first and second hinges while the cover can be held in its closed position with the force produced by the first hinge. Also, the first hinge produces an auxiliary force to facilitate cover-opening action, and the forces produced by the first and second hinges serve to prevent the falling of the cover during its closing motion. When the cover is opened or closed, the force produced by the first hinge reverses (from cover-opening to closing direction or from cover-closing to opening direction) at a specific angle of the cover due to a cam mechanism of the first hinge. This construction of the invention is advantageous in that the second hinge produces the force acting on the cover in a direction opposite to the direction of its swing motion, thereby preventing a sudden change in the motion of the cover and enabling smooth cover-opening and closing actions.

According to this construction, it is possible to equip the analyzing apparatus with a cover holding mechanism by just making small spaces available for attaching the hinges without the need for larger dedicated spaces for gas dampers, for example, enabling a reduction in the size of the apparatus.

In yet another feature of the invention, the analyzing apparatus further comprises at least two hinges provided between the housing and a cover covering a top surface of the housing, the hinges supporting the cover in a manner that the cover can be freely opened and closed and held at a desired position, wherein at least one of the hinges is a spring cam hinge including a cam mechanism and a spring capable of producing a force acting on the cover in its opening or closing direction, the direction of the force reversing at a specific angle of the cover halfway between its open and closed positions, and at least another one of the hinges is a friction hinge capable of producing a frictional force which works to hold the cover at any position between its open and closed positions.

This construction employing a combination of the spring cam hinge and the friction hinge makes it possible take advantage of the earlier-mentioned three types of cover holding mechanisms, that is, the gas damper, spring-cam-hinge, and friction-hinge mechanisms. Specifically, the cover can be held in its open position with the force produced by the spring and the frictional force produced by the friction hinge while the cover can be held in its closed position with the forces produced by the cam mechanism and the spring. Also, the spring produces an auxiliary force to facilitate cover-opening action, and the forces produced by the cam mechanism and the spring serve to prevent the falling of the cover during its closing motion. When the cover is opened or closed, the force produced by the spring cam hinge reverses (from cover-closing to opening direction or from cover-opening to closing direction) at a specific angle of the cover due to a cam mechanism. This construction of the invention is advantageous in that the friction hinge produces the frictional force acting on the cover in a direction opposite to the direction of its swing motion, thereby preventing a sudden change in the motion of the cover and enabling smooth cover-opening and closing actions.

In another form of the invention, an analyzing apparatus comprises a reagent unit, a cooling device for cooling the reagent unit, a sample storage unit, a reaction unit, a control unit for controlling the individual units and device, a housing enclosing the individual units and device, and at least two hinges provided between the housing and a cover covering a top surface of the housing, the hinges supporting the cover in a manner that the cover can be freely opened and closed and held at a desired position. In this analyzing apparatus, at least one of the hinges is a first hinge which produces a force acting on the cover in its opening or closing direction, the direction of the force reversing at a specific position of the cover, and at least another one of the hinges is a second hinge which produces a force acting on the cover in a direction opposite to the direction of its swing motion.

According to this construction, it is possible to equip the analyzing apparatus with a cover holding mechanism by just making small spaces available for attaching the hinges without the need for larger dedicated spaces for gas dampers, for example, enabling a reduction in the size of the apparatus. Since the two types of hinges (spring cam hinge and friction hinge) are less susceptible to the effect of aging and need not be periodically replaced, their use leads to a reduction in industrial waste product. Furthermore, both the spring cam hinge and the friction hinge are less expensive compared to the gas dampers, resulting in a reduction in overall manufacturing cost of the apparatus.

In the analyzing apparatus thus constructed, the cover would not be automatically brought to its fully open or closed position from a position halfway between the open and closed positions by the own weight of the cover and the force produced by the spring. Therefore, this construction of the invention is advantageous in that the cover can be held at a desired position by properly balancing the force of the spring and the frictional resistance.

These and other objects, features and advantages of the invention will become more apparent upon reading the following detailed description in conjunction with the accompanying drawings.

DETAILED DESCRIPTION OF THE PREFERRED EMBODIMENTS OF THE INVENTION

A first embodiment of the invention is described with reference to FIGS. 1 to 3.

Figure 1:
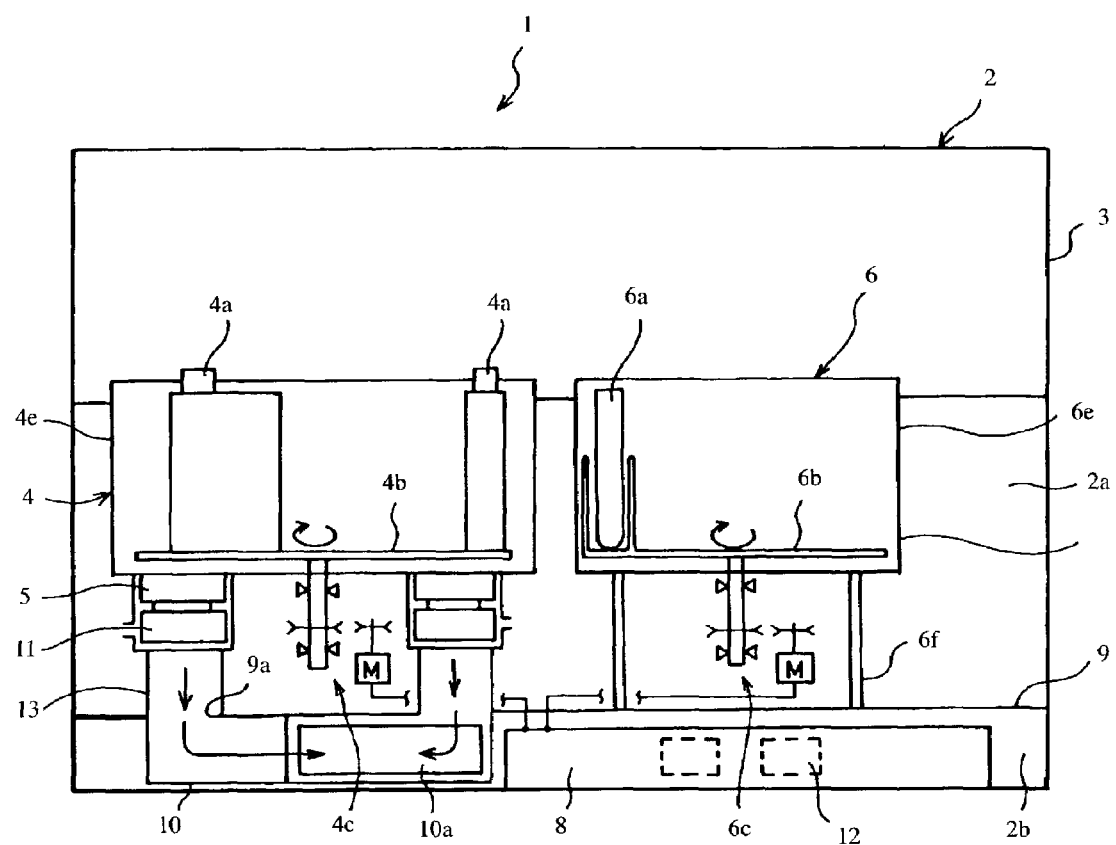
FIG. 1 is a vertical cross section of an analyzing apparatus according to a first embodiment of the invention.
Figure 2:
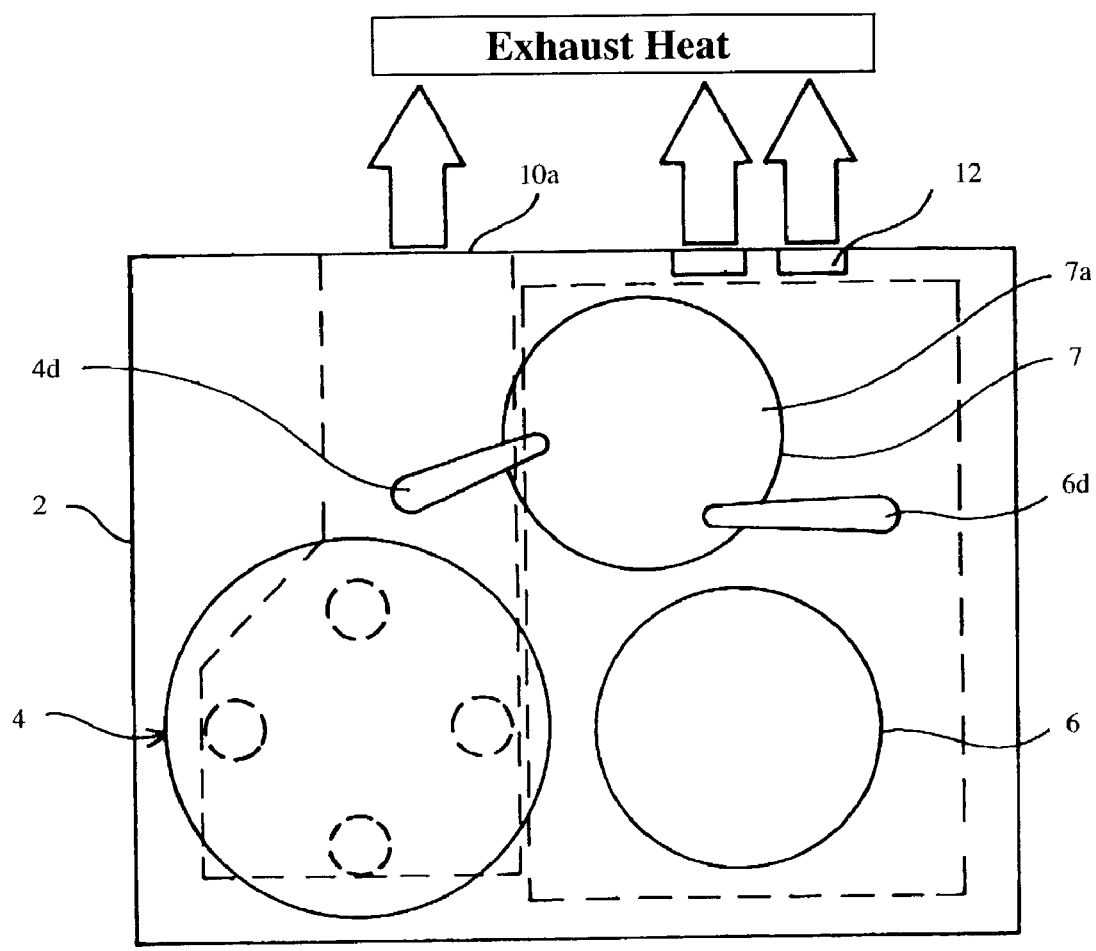
FIG. 2 is a plan view of the analyzing apparatus of FIG. 1.
Figure 3:
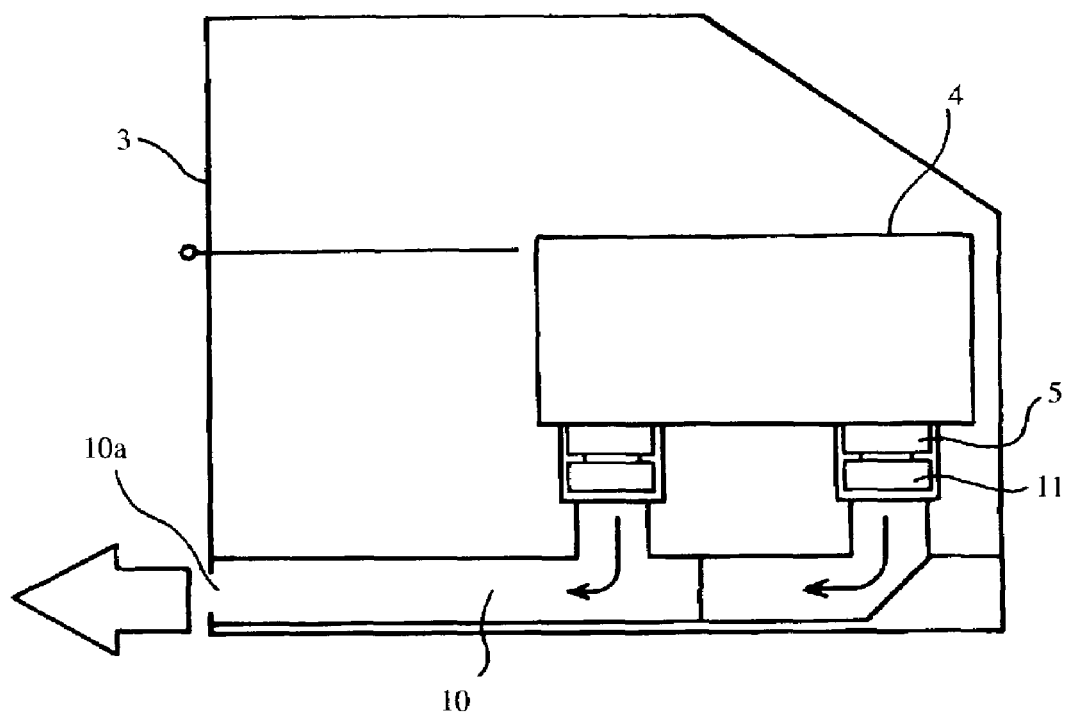
FIG. 3 is a vertical cross section of a reaction unit, cooling devices and a duct of the analyzing apparatus of FIG. 1.

As shown in FIGS. 1 and 2, analyzing apparatus 1 according to the first embodiment of the invention comprises a reagent unit 4, cooling devices 5 for cooling the reagent unit 4, a sample storage unit 6, a reaction unit 7 and a power supply/control unit 8 for feeding electric power to and controlling the individual units contained in a housing 2. A cover 3 which can be opened and closed is attached to the housing 2.

The interior of the housing 2 is divided into an upper space 2a and a lower space 2b by a partition 9 which is formed of a flat iron plate having through holes 9a connecting to a later-described duct 10. The upper space 2a of the partition 9 forms a low-temperature area. The upper space 2a of the housing 2 contains the reagent unit 4, the cooling devices 5 for cooling the reagent unit 4, the sample storage unit 6 and the reaction unit 7. The lower space 2b of the partition 9 forms a high-temperature area. The lower space 2b of the housing 2 contains the duct 10 for collecting exhaust heat from the cooling devices 5 and the power supply/control unit 8.

The reagent unit 4 is formed of reagent bottles 4a, a reagent tray 4b, a tray turning mechanism 4c, a container 4e and the cooling devices 5. The reagent tray 4b carries a plurality of reagent bottles 4a. The tray turning mechanism 4c provided beneath the reagent tray 4b is linked to a central bottom part of the reagent tray 4b. The tray turning mechanism 4c turns the reagent tray 4b such that the desired reagent bottle 4a is positioned at a sucking position of a pipette 4d as shown in FIG. 2. Attached to the bottom of the container 4e, the cooling devices 5 are operated to cool the reagent unit 4 continuously or when the temperature within the container 4e has increased so as to maintain a constant temperature inside the container 4e.

The container 4e is fixed to the partition 9 with cylindrical structures 13 containing the individual cooling devices 5, which are formed of Peltier elements, for example, placed between the container 4e and the partition 9. Each cylindrical structure 13 is joined to the corresponding hole 9a in the partition 9. The duct 10 connected to the exterior of the housing 2 is joined to a lower end of each cylindrical structure 13 containing the cooling device 5, that is, to the bottom side of each hole 9a. As shown in FIG. 1, the duct 10 has an exhaust air outlet 10a and the cooling devices 5 are provided with individual exhaust fans 11. Connected to the exterior of the housing 2 through the exhaust air outlet 10a, the duct 10 collects exhaust heat generated by the cooling devices 5 and forces the exhaust heat to the exterior through the exhaust air outlet 10a which is made in the lower space 2b of the housing 2. The exhaust fans 11 are provided beneath the respective cooling devices 5 to forcibly remove the exhaust heat generated by the cooling devices 5 together with an air flow which flows from inside the housing 2 through the individual cylindrical structures 13, the holes 9a in the partition 9 and the duct 10. As shown in FIG. 2, the duct 10 connects to the multiple (four in the illustrated example) cooling devices 5 to collect the exhaust heat from them. The exhaust heat is forced to the exterior of the housing 2 through the duct 10 and the exhaust air outlet 10a. It is preferable to cover the inside or outside surface of the duct 10 with a heat insulation material to prevent the heat from being conducted to the upper space 2a through the wall of the duct 10 and the partition 9.

The sample storage unit 6 is formed of samples 6a, a sample tray 6b, a tray turning mechanism 6c and a container 6. The samples 6a are kept in blood retaining tubes held on the sample tray 6b. The tray turning mechanism 6c provided beneath the sample tray 6b is linked to a central bottom part of the sample tray 6b. The tray turning mechanism 6c turns any desired sample 6a to the sucking position of a pipette 6d as shown in FIG. 2. The container 6e is fixed to the top of the partition 9 by supporting bars 6f.

Referring to FIG. 2, the reaction unit 7 includes a cuvette table 7a in addition to a plurality of cuvettes, a table turning mechanism, a table turning mechanism and a container which are not illustrated. Carrying the cuvettes on the cuvette table 7a, the reaction unit 7 accelerates reaction between a reagent and the samples 6a discharged respectively from the pipette 4d and the pipette 6d into the cuvettes. The table turning mechanism provided beneath the container is linked to a central bottom part of the cuvette table 7a to turn any desired cuvette to an injecting position.

The power supply/control unit 8 includes the tray turning mechanism 4c of the reagent unit 4, the tray turning mechanism 6c of the sample storage unit 6, a driver for turning a motor of the table turning mechanism (not shown) of the reaction unit 7 as well as power supply/control circuitry for the individual units. The power supply/control unit 8 is accommodated in the lower space 2b of the housing 2. As shown in FIG. 2, exhaust fans 12 are provided on the back of the lower space 2b containing the power supply/control unit 8. These exhaust fans 12 creates an air flow inside the lower space 2b of the housing 2 flowing at least along the power supply/control unit 8 to remove the exhaust heat generated by the power supply/control unit 8 to the exterior of the housing 2.

As shown in the foregoing discussion, it is made possible in the analyzing apparatus 1 of the first embodiment to avoid adverse effects of the heat generated by the power supply/control unit 8 and the cooling devices 5 for cooling the reagent unit 4 provided in the upper space 2a of the housing 2 and to accomplish efficient cooling of the reagent unit 4 by dividing the interior of the housing 2 into the upper space 2a (low-temperature area) and the housing 2c (high-temperature area). While motors of the turning mechanisms of the individual units are contained in the upper space 2a of the housing 2, heat generated by the motors is exhausted from the housing 2 with sucked air flows produced by the exhaust fans 11 and the cooling capacity of the cooling devices 5 exceeds the amount of heat generated by the motors, so that it is not necessary to ventilate the upper space 2a of the housing 2. This makes it possible to obtain an improved heat exhaust efficiency. Furthermore, the embodiment makes it possible to decrease the size of the lower space 2b to a minimum since the lower space 2b contains a minimum number of components, such as the power supply/control unit 8 containing the power supply/control circuitry and motor drivers for the turning mechanisms of the individual units and the duct 10, which require removal of exhaust heat. Thus, the present embodiment simplifies the structure of the housing 2, facilitates arrangement of the turning mechanisms within the housing 2 and decreases overall manufacturing costs.

While the invention has been described with reference to one preferred embodiment, the invention is not limited thereto but various design changes are possible within the spirit and scope of the invention as recited in the appended claims. For example, the cooling device 5 may be ventilated without using the exhaust fans 11. The heat generated by the power supply/control unit 8 may also be exhausted without using the exhaust fans 12. Furthermore, it is not absolutely necessary to provide the common duct 10 for the multiple cooling devices 5. Instead, a plurality of ducts may be provided for ventilating the individual cooling devices 5.

Figure 4:
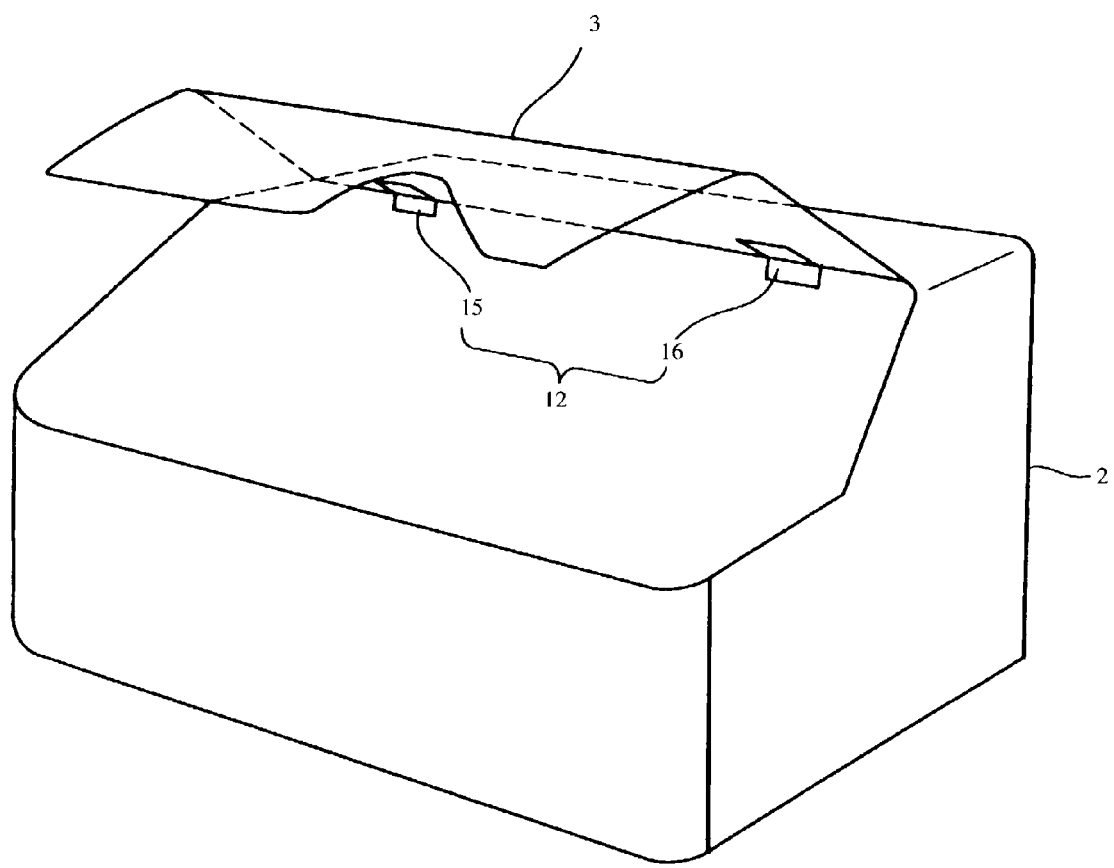
FIG. 4 is a perspective view of an analyzing apparatus provided with a cover holding mechanism according to a second embodiment of the invention.

A second embodiment of the invention is now described referring to FIGS. 4 to 11. A cover holding mechanism 14 of this embodiment including a spring cam hinge 15 and a friction hinge 16 is provided between a housing 2 and a cover 3 covering a top surface of the housing 2 as shown in FIG. 4.

Figure 5:
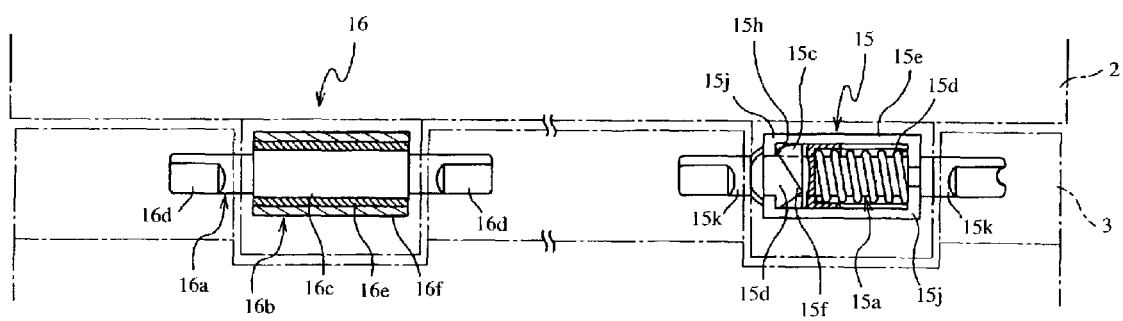
FIG. 5 is a cross section of the cover holding mechanism according to the second embodiment.
Figure 6A:
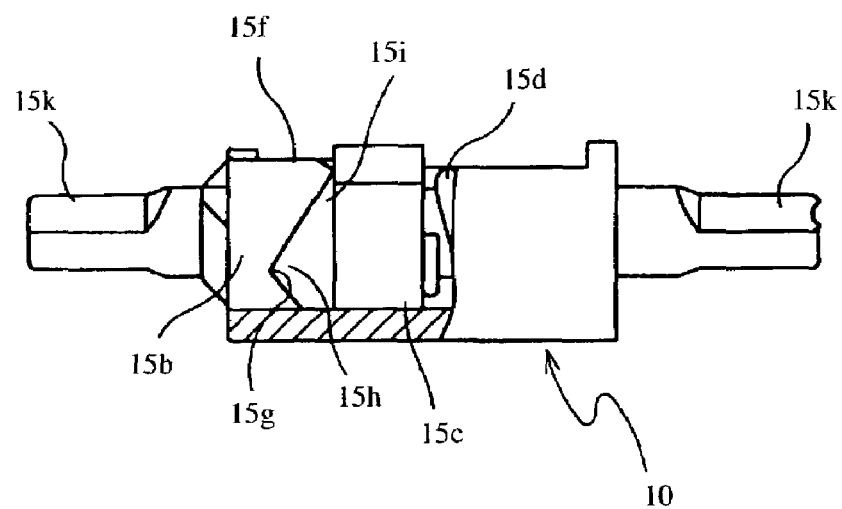
FIGS. 6A, 6B and 6C are a cross section, a left side view and a right side view of a spring cam hinge of the cover holding mechanism of the second embodiment.
Figure 6B:
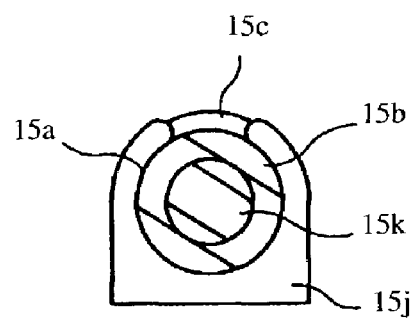
Figure 6C:
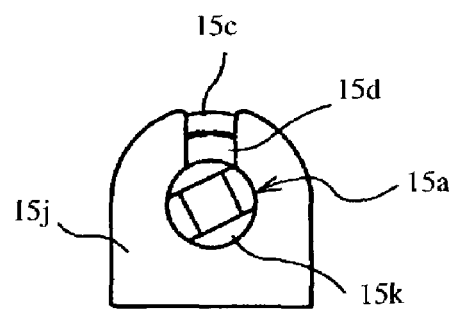
Figure 7:
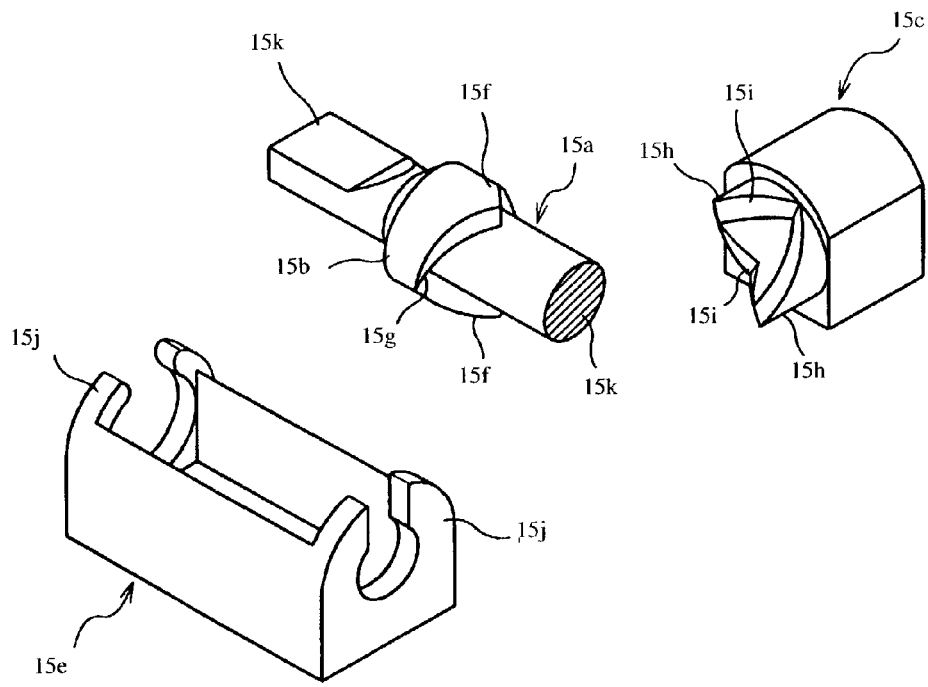
FIG. 7 is an exploded perspective view of the spring cam hinge of the cover holding mechanism of the second embodiment.
Figure 8:
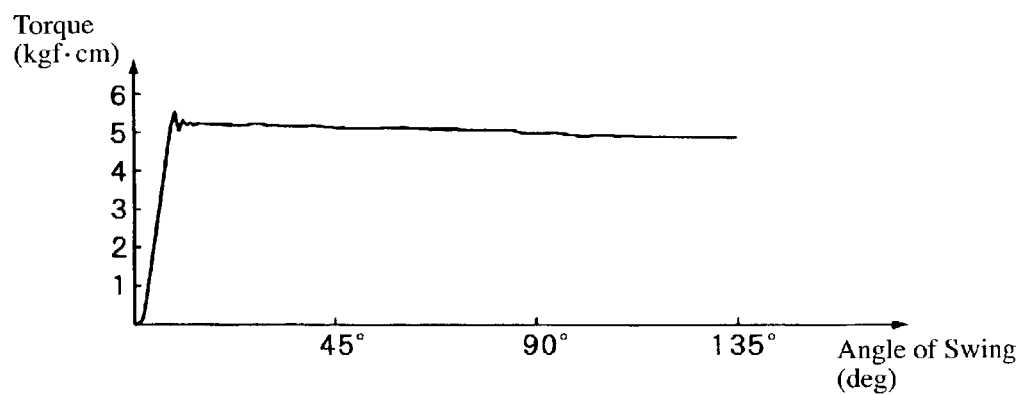
FIG. 8 is a diagram showing a characteristic of a friction hinge of the cover holding mechanism of the second embodiment with respect to the angle of swing motion and torque.

The spring cam hinge 15 includes a shaft member 15a, a first cam 15b, a second cam 15c, a spring 15d and a case 15e enclosing the elements 15a-15d as shown in FIG. 5. As will be later described in detail, both end portions 15k of the shaft member 15a projecting out of the case 15e are fixed to the cover 3 while the case 15e is fixed to the housing 2.

As shown in FIGS. 6A-6C and 7, the shaft member 15a having a rotational axis about which the shaft member 15a can rotate is supported by both end walls 15j of the case 15e. Having an overall length larger than the distance between the end walls 15j of the case 15e, the two end portions 15k of the shaft member 15a extend outward from the case 15e. In this way, the shaft member 15a is rotatably supported by the case 15e in its internal space. The first cam 15b is provided as an integral part of the shaft member 15a on its cylindrical outer surface. The second cam 15c is fitted over the cylindrical outer surface of the shaft member 15a at a position located on the inside of the case 15e in such a manner that the second cam 15c can rotate relative to the shaft member 15a and move along its axial direction but does not rotate relative to the case 15e. The spring 15d is fitted over the shaft member 15a which is held in a compressed state between the second cam 15c and one of the end walls 15j of the case 15e. The first cam 15b and the second cam 15c continuously push the spring 15d against its elastic force. A contact surface of the first cam 15b has two each ridges 15f and V-shaped grooves 15g alternately arranged along the circumference of the first cam 15b, while a contact surface of the second cam 15c also has two each ridges 15h and V-shaped grooves 15i alternately arranged along the circumference of the second cam 15c, in which the ridges 15f and the grooves 15g of the first cam 15b engage with the grooves 15i and the ridges 15h of the second cam 15c, respectively.

As the ridges 15f and the grooves 15g of the first cam 15b mesh with the grooves 15i and the ridges 15h of the second cam 15c as stated above, the cover 3 is held in its open and closed positions in a stable fashion. The open position of the cover 3 is a position where the cover 3 makes an angle smaller than 90 degrees with the housing 2. The first cam 15b and the second cam 15c are arranged such that their ridges 15f, 15h and grooves 15g, 15i mesh with one another at this open position of the cover 3. The closed position of the cover 3 is a position where the cover 3 makes a zero-degree angle with the housing 2. The first cam 15b and the second cam 15c are arranged such that their ridges 15f, 15h and grooves 15g, 15i mesh with one another at this closed position of the cover 3.

When the cover 3 is swung from the open position to the closed position, or vice versa, the first cam 15b rotates together with the shaft member 15a and, as a consequence, the spring 15d forces the second cam 15c against the first cam 15b, causing slanting surfaces between the grooves 15i and the ridges 15h of the second cam 15c to press against slanting surfaces between the ridges 15f and the grooves 15g of the first cam 15b. Until the ridges 15f of the first cam 15b pass over the ridges 15h of the second cam 15c, the ridges 15f of the first cam 15b move toward their original positions where they mesh with the grooves 15i of the second cam 15c due to pushing force of the spring 15d. Also when the cover 3 is swung from the open position to and beyond the closed position, or vice versa, the ridges 15f of the first cam 15b pass over the ridges 15h of the second cam 15c and, then, due to the pushing force of the spring 15d, the ridges 15f of the first cam 15b move toward positions where they mesh with the grooves 15i of the adjacent second cam 15c.

The friction hinge 16 includes a shaft member 16a and a swing motion support 16b as shown in FIG. 5. As will be later described in detail, both end portions 16d of the shaft member 16a are fixed to the cover 3 and a case 16f is fixed to the housing 2. The shaft member 16a is formed of a large-diameter portion 16c, which comes into contact with the swing motion support 16b and constitutes a rotary shaft serving as an axis of swing motion, and the end portions 16d having a smaller diameter than the large-diameter portion 16c. The large-diameter portion 16c of the shaft member 16a has a machined outer surface to ensure smooth sliding contact. The shaft member 16a has a larger overall length than the swing motion support 16b with the two end portions 16d of the shaft member 16a projecting outward from both ends of the swing motion support 16b. The swing motion support 16b holds in its through hole the rotary shaft portion of the shaft member 16a in a manner that the shaft member 16a can be turned to a desired angle of swing motion about its rotary shaft portion. The swing motion support 16b is formed of a resin member 16e and the case 16f. The resin member 16e forms a surface which comes into direct contact with the shaft member 16a. The case 16f is integrally formed with the resin member 16e on its outside.

More specifically, the resin member 16e and the case 16f are one-piece molded by forcing the resin member 16e into the case 16f which has been placed in advance in a high-temperature metal die, for example. According to this method, the resin member 16e shrinks when the resin member 16e and the case 16f cool down after the molding process. Then, the resin member 16e is tightly fitted in the case 16f by stress occurring due to interference between the resin member 16e and the case 16f.

The outer surface of the rotary shaft portion of the shaft member 16a is machined in advance as stated above. If the surface roughness of the rotary shaft portion is 0.18 micrometers, for example, the shaft member 16a exhibits a characteristic shown in FIG. 8 with respect to the relationship between the angle of swing motion and torque. Accordingly, the swing motion support 16b which has been brought into close contact with the shaft member 16a due to molding and shrinkage of the resin member 16e produces a large frictional resistance acting against a turning force of the shaft member 16a at their contact surface. When a large external torque acting against the frictional resistance between the shaft member 16a and the swing motion support 16b is applied to the shaft member 16a, the shaft member 16a turns relative to the swing motion support 16b. When the applied torque is smaller than the frictional resistance, however, the shaft member 16a not turn at all. Thus, the cover 3 can be held at a desired angle of its swing motion by the frictional resistance.

The cover holding mechanism 14 including the spring cam hinge 15 and the friction hinge 16 holds the cover 3 at any desired position between about 30% to 70% of full excursion of the cover 3 from its fully open position to fully closed position, and vice versa. To make this possible, the spring 15d of the spring cam hinge 15 is adjusted and the outer surface of the shaft member 16a is pretreated such that frictional resistance produced by the friction hinge 16 becomes larger than a combination of the force produced by the spring 15d of the spring cam hinge 15 and the weight of the cover 3. The adjustment of the spring 15d of the spring cam hinge 15 and surface treatment of the spring 15d of the spring cam hinge 15 are controlled in such a manner that the frictional resistance produced by the friction hinge 16 becomes smaller than the combination of the force produced by the spring 15d of the spring cam hinge 15 and the weight of the cover 3 in order to produce an auxiliary force facilitating cover-opening and closing actions and to smoothen opening and closing motions of the cover 3 in ranges other than the aforementioned 30% to 70% of the full excursion of the cover 3.

Figure 9A:
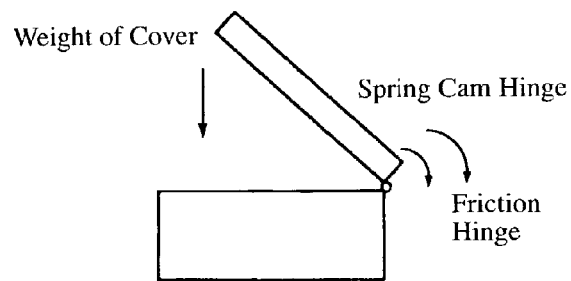
FIGS. 9A to 9D are side views showing the operation of the cover holding mechanism of the second embodiment as a cover of an analyzing apparatus is in a fully open position, a fully closed position, a position halfway from the closed position to the open position, and a position halfway from the open position to the closed position, respectively.

As so far described, the spring cam hinge 15 and the friction hinge 16 exert forces for supporting the cover 3 when it is in the fully open position as shown in FIG. 9A in the analyzing apparatus 1 of the present embodiment. Specifically, as the ridges 15f and the grooves 15g of the first cam 15b mesh with the grooves 15i and the ridges 15h of the second cam 15c and the spring 15d exerts its pushing force at the fully open position of the cover 3, the spring cam hinge 15 produces a force acting on the cover 3 in its further opening direction. If the weight of the cover 3 is larger than the force produced by the spring cam hinge 15, the cover 3 might be caused to close. Since the friction hinge 16 produces a frictional force in a direction opposite to the closing direction of the cover 3, however, the cover 3 can be held in its open position.

Figure 9B:
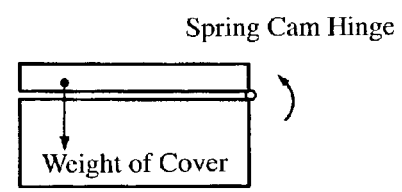

In the closed position of the cover 3 shown in FIG. 9B, the spring cam hinge 15 exerts its force acting on the cover 3. Specifically, as the ridges 15f and the grooves 15g of the first cam 15b mesh with the grooves 15i and the ridges 15h of the second cam 15c and the spring 15d exerts its pushing force in this position, the spring cam hinge 15 exerts the force acting in the closing direction of the cover 3, so that the cover 3 remains in its closed position without opening.

Figure 9C:
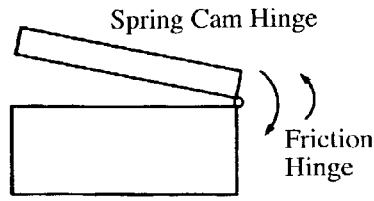

When the cover 3 is being opened as shown in FIG. 9C, both the spring cam hinge 15 and the friction hinge 16 exert their forces. Specifically, as the ridges 15f and the grooves 15g of the first cam 15b are not in mesh with the grooves 15i and the ridges 15h of the second cam 15c and the spring 15d presses the second cam 15c against the first cam 15b in this condition, the spring 15d produces an auxiliary force acting on the cover 3 in its opening direction, causing the ridges 15f and the grooves 15g of the first cam 15b to mesh with the grooves 15i and the ridges 15h of the second cam 15c at a desired angle of the cover 3. As the spring cam hinge 15 produces a force acting in the opening direction of the cover 3 in this fashion, the cover 3 might be caused to further open if the force produced by the spring cam hinge 15 overwhelms the weight of the cover 3. Since the friction hinge 16 produces a frictional force in a direction opposite to the opening direction of the cover 3, however, the cover 3 can be held at its current position.

Figure 9D:
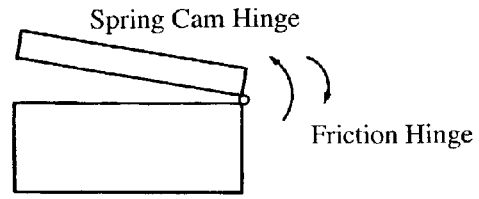

When the cover 3 is being closed as shown in FIG. 9D, both the spring cam hinge 15 and the friction hinge 16 exert their forces. Specifically, as the ridges 15f and the grooves 15g of the first cam 15b are not in mesh with the grooves 15i and the ridges 15h of the second cam 15c and the spring 15d presses the second cam 15c against the first cam 15b in this condition, the spring 15d produces an auxiliary force acting on the cover 3 in its closing direction, causing the ridges 15f and the grooves 15g of the first cam 15b to mesh with the grooves 15i and the ridges 15h of the second cam 15c at a desired angle of the cover 3. As the spring cam hinge 15 produces a force acting in the closing direction of the cover 3 in this fashion, the cover 3 might be caused to close due to its own weight. Since the friction hinge 16 produces a frictional force in a direction opposite to the closing direction of the cover 3, however, the friction hinge 16 holds the cover 3 at its current position or serves to smoothen the movement of the cover 3.

It would be appreciated from the foregoing discussion that the spring cam hinge 15 serves to assist in cover-opening and closing actions and to hold the cover 3 at its closed position while the friction hinge 16 serves to produce a force in a direction opposite to the moving direction of the cover 3, hold the cover 3 at its current position and smoothen the movement of the cover 3. It is also possible to cause the cover 3 to automatically open and close by properly adjusting the balance between individual forces.

While the invention has been described with reference to its preferred embodiments, the invention is not limited thereto but various design changes are possible within the spirit and scope of the invention as recited in the appended claims. For example, the spring cam hinge 15 may be constructed such that both end portions 15*k* of the shaft member 15*a* are fixed to the housing 2 and the case 15*e* is fixed to the cover 3. Also, the friction hinge 16 may be constructed such that both end portions 16*d* of the shaft member 16*a* are fixed to the housing 2 and the case 16*f* is fixed to the cover 3.

Furthermore, the cover holding mechanism 14 may be constructed of more than one each spring cam hinge 15 and friction hinge 16 to achieve a proper balance between forces acting in the cover holding mechanism 14. For example, the cover holding mechanism 14 may include one spring cam hinge 15 at a central position and two friction hinges 16 provided on both sides of the spring cam hinge 15.

Figure 10:
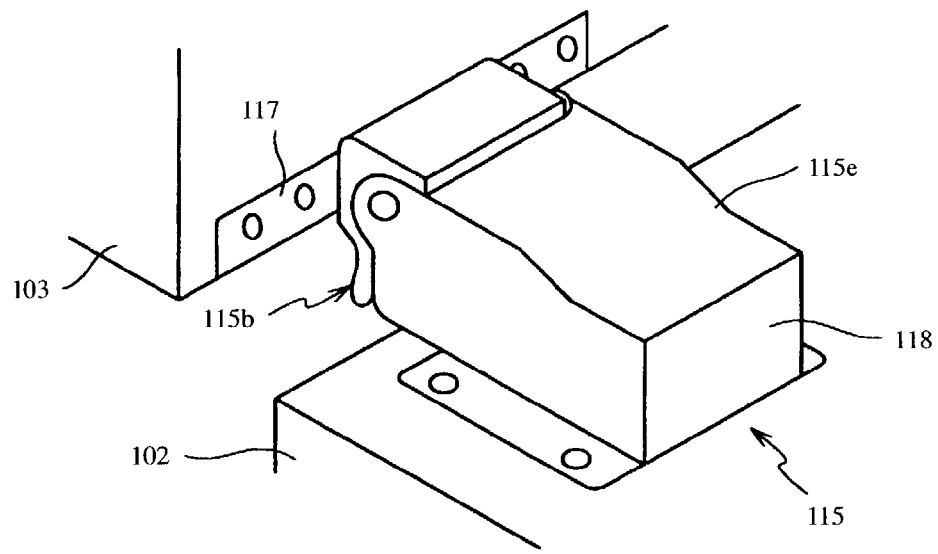
FIG. 10 is a perspective view particularly showing a spring cam hinge of a cover holding mechanism according to a third embodiment of the invention.
Figure 11:
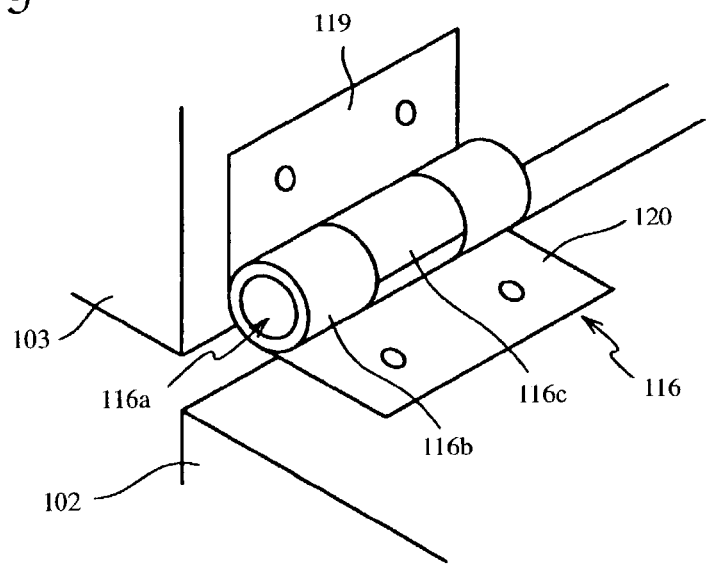
FIG. 11 is a perspective view particularly showing a friction hinge of the cover holding mechanism according to the third embodiment of the invention.

A cover holding mechanism employing a spring cam hinge 115 and a friction hinge 116 according to a third embodiment of the invention is now described referring to FIGS. 10 and 11. The spring cam hinge 115 includes a first hinge plate 117 and a second hinge plate 118 which are fixed to a cover 103 and a housing 102, respectively, as shown in FIG. 10. The first hinge plate 117 includes a first cam 115*b* while the second hinge plate 118 includes a case 115*e* enclosing a shaft member, a second cam and a spring which are not illustrated, wherein the shaft member is arranged at right angles to the surface of the cover 103. The first hinge plate 117 is fixed to the exterior of the cover 103 (or the housing 102) and the second hinge plate 118 is fixed to the exterior of the housing 102 (or the cover 103) as illustrated.

Provided between the housing 102 and the cover 103, the friction hinge 116 includes a first hinge plate 119 and a second hinge plate 120 as shown in FIG. 11. The first hinge plate 119 includes a shaft member 116*a* which constitutes a rotary shaft serving as an axis of swing motion and a swing motion support 116*b* which supports the shaft member 116*a* by its both end portions. The second hinge plate 120 includes the shaft member 116*a* and a swing motion support 116*c* which supports the shaft member 116*a* by its central portion. The shaft member 116*a* is fixed to the swing motion support 116*c* and produces a frictional resistance when turning relative to the swing motion support 116*b*. The first hinge plate 119 is fixed to the exterior of the cover 103 (or the housing 102) and the second hinge plate 120 is fixed to the exterior of the housing 102 (or the cover 103) as illustrated.

While the cover holding mechanism of this embodiment employs the spring cam hinge 115 as a first hinge and the friction hinge 116 as a second hinge, the invention is not limited thereto but may employ other types of hinges.

Figure 12A:
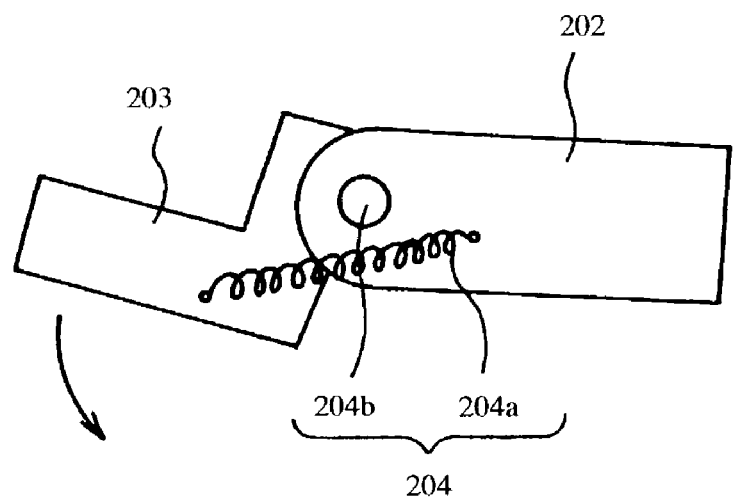
FIGS. 12A and 12B are side views showing the operation of a cover holding mechanism including a spring and a link in one variation of the invention, in which a cover is in a position halfway from a closed position to an open position, and in a position halfway from the open position to the closed position, respectively.
Figure 12B:
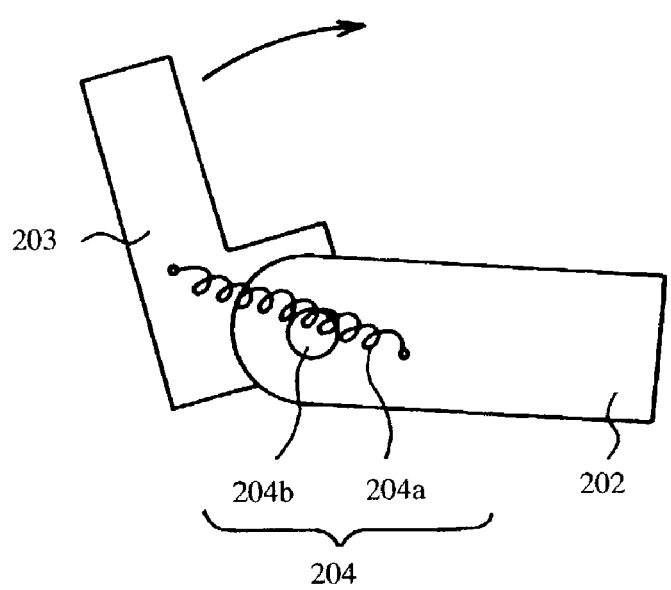

In one variation of the invention, a mechanism 204 including a spring 204*a* and a link 204*b* is used as a first hinge as shown in FIGS. 12A and 12B. In this cover holding mechanism 204 formed of the housing 24*a* and the link 204*b*, both ends of the spring 204*a* are joined to a housing 202 and a cover 20. The link 204*b* passes through walls of the housing 202 and the cover 203 in a manner that the cover 203 can be freely opened and closed by swing motion about the link 204*b*. In a condition shown in FIG. 12A, the spring 204*a* exerts a force acting on the cover 203 in its opening direction so that the cover 203 is held in its open position. In a condition shown in FIG. 12B, on the other hand, the direction of the force exerted by the spring 204*a* reverses to the cover-closing direction at a specific angle of the cover 203 so that the cover 203 is biased to the closing direction.

Figure 13:
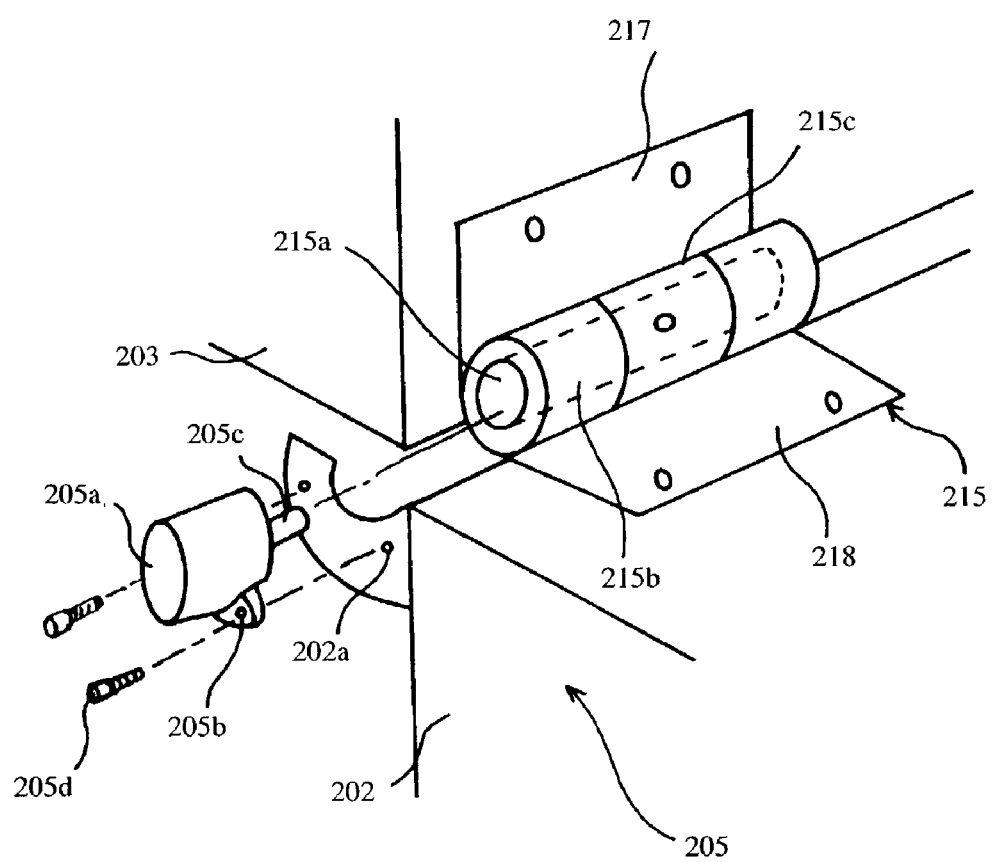
FIG. 13 is a perspective view showing a hinge mechanism used as a second hinge employing a rotary damper in another variation of the invention.

In another variation of the invention, a hinge mechanism 205 formed of a combination of a rotary damper 205*a* and a hinge 215 shown in FIG. 13 is used as a second hinge. As shown in FIG. 13, the rotary damper 205*a* is formed of a main body portion 205*b* and a shaft portion 205*c*. This rotary damper 205*a* produces a force acting on a cover 203 in a direction opposite to the direction of its swing motion by use of viscosity of oil. The main body portion 205*b* of the rotary damper 205*a* is fixed to a housing 202 as the main body portion 205*b* is inserted into holes 202*a* and fastened by screws 205*d*. On the other hand, the shaft portion 205*c* of the rotary damper 205*a* is fitted into a shaft member 215*a* of the hinge 215 and fixed thereto. The hinge 215 provided between the housing 202 and the cover 203 includes a first hinge plate 217 and a second hinge plate 218. The hinge 215 is constructed such that the first hinge plate 217 and the second hinge plate 218 can be freely swung about the shaft member 215*a*. A swing motion support 215*c* fixing the shaft member 215*a* is provided on the first hinge plate 217 which is fixed to the cover 203. A swing motion support 215*b* holding both ends of the shaft member 215*a* is provided on the second hinge plate 218 which is fixed to the housing 202.

When the cover 203 is opened or closed in the aforementioned construction, the shaft member 215*a* fixed to the first hinge plate 217 turns together with the cover 203 and the shaft portion 205*c* of the rotary damper 205*a* fixed to the shaft member 215*a* turns together with the shaft member 215*a*. On the other hand, the main body portion 205*b* of the rotary damper 205*a* fixed to the housing 202 remains in its fixed position even when the cover 203 is opened or closed. Since the rotary damper 205*a* is constructed such that a frictional resistance occurs between the main body portion 205*b* and the shaft portion 205*c* in this way when the cover 203 is swung, the rotary damper 205*a* produces a force acting on the cover 203 in a direction opposite to its swing direction.

What is claimed is:

1. An analyzing apparatus whose interior is divided into an upper space and lower space, further comprising:
    a set of elements contained within the upper space, including:
        a reagent unit,
        a cooling device for cooling said reagent unit,
        a sample storage unit, and
        a reaction unit;
    a power supply/control unit contained within the lower space, said power supply/control unit for feeding electric power to and controlling said set of elements;
    a housing enclosing said set of elements and power supply/control unit;
    a partition dividing the interior of said housing into the upper space and the lower space; and
    at least two hinges provided between said housing and a cover covering a top surface of said housing, said hinges supporting the cover in a manner that the cover can be freely opened and closed and held at a desired position;

wherein at least one of said hinges is a first hinge which produces a force acting on the cover in its opening or closing direction, the direction, the direction of the force reversing at a specific position of the cover, and at least another one of said hinges is a second hinge which produces a force acting on the cover in a direction opposite to the direction of its swing motion.

2. An analyzing apparatus whose interior is divided into an upper space and lower space, comprising:

a set of elements contained within the upper space, including:
a reagent unit,
a cooling device for cooling said reagent unit,
a sample storage unit, and
a reaction unit;

a power supply/control unit contained within the lower space, said power supply/control unit for feeding electric power to and controlling said set of elements;

a housing enclosing said set of elements and power supply/control unit;

a partition dividing the interior of said housing into the upper space and the lower space; and at least two hinges provided between said housing and a cover covering a top surface of said housing, said hinges supporting the cover in a manner that the cover can be freely opened and closed and held at a desired position;

wherein at least one of said hinges is a spring cam hinge including a cam mechanism and a spring capable of producing a force acting on the cover in its opening or closing direction, the direction of the force reversing at a specific angle of the cover halfway between its open and closed positions, and at least another one of said hinges is a friction hinge capable of producing a frictional force which works to hold the cover at any position between its open and closed positions.

3. An analyzing apparatus whose interior is divided into an upper space and lower space, comprising:

a set of elements contained within the upper space, including:
a reagent unit,
a cooling device for cooling said reagent unit,
a sample storage unit, and
a reaction unit;

a power supply/control unit contained within the lower space, said power supply/control unit for feeding electric power to and controlling said set of elements;

a housing enclosing said set of elements and power supply/control unit;

a partition dividing the interior of said housing into the upper space and the lower space; and at least two hinges provided between said housing and a cover covering a top surface of said housing, said hinges supporting the cover in a manner that the cover can be freely opened and closed and held at a desired position;

wherein at least one of said hinges is a spring cam hinge including a cam mechanism and a spring capable of producing a force acting on the cover in its opening or closing direction, the direction of the force reversing at a specific angle of the cover halfway between its open and closed positions, and at least another one of said hinges is a friction hinge capable of producing a frictional force which works to hold the cover at any position between its open and closed positions; and wherein a cover-opening or closing force due to the sum of the force produced by the spring cam hinge and the weight of the cover is smaller than the frictional force produced by the friction hinge at any position of the cover between its open and closed positions.

4. An analyzing apparatus comprising:

a set of elements, including:
a reagent unit,
a cooling device for cooling said reagent unit,
a sample storage unit, and
a reaction unit;

a control unit for controlling said set of elements;

a housing enclosing said set of elements and control unit; and at least two hinges provided between said housing and a cover covering a top surface of said housing, said hinges supporting the cover in a manner that the cover can be freely opened and closed and held at a desired position;

wherein at least one of said hinges is a first hinge which produces a force acting on the cover in its opening or closing direction, the direction of the force reversing at a specific position of the cover, and at least another one of said hinges is a second hinge which produces a force acting on the cover in a direction opposite to the direction of its swing motion.

\* \* \* \* \*